United States Patent [19]

Küpper et al.

[11] Patent Number: 5,292,970
[45] Date of Patent: Mar. 8, 1994

[54] METHOD OF MANUFACTURING ORTHO-SUBSTITUTED ALKYLPHENOLS, AND CATALYST THEREFOR

[75] Inventors: Friedrich-Wilhelm Küpper; Wolfgang Müller, both of Marl, Fed. Rep. of Germany

[73] Assignee: Huels Aktiengesellschaft, Marl, Fed. Rep. of Germany

[21] Appl. No.: 983,048

[22] Filed: Nov. 30, 1992

[30] Foreign Application Priority Data

Nov. 28, 1991 [DE] Fed. Rep. of Germany ....... 4139056

[51] Int. Cl.$^5$ .............................................. C07C 37/14
[52] U.S. Cl. ..................................... 568/794; 568/790
[58] Field of Search ............... 568/794, 789, 784, 790

[56] References Cited

U.S. PATENT DOCUMENTS

| | | | |
|---|---|---|---|
| 2,831,898 | 4/1958 | Ecke et al. | 568/794 |
| 4,870,215 | 9/1989 | Wiker et al. | 568/794 |
| 5,091,594 | 2/1992 | Küpper et al. | 568/794 |

*Primary Examiner*—Werren B. Lone

*Attorney, Agent, or Firm*—Oblon, Spivak, McClelland, Maier & Neustadt

[57] ABSTRACT

A method of manufacturing orthosubstituted alkylphenols, employing a catalyst of increased activity, by reacting phenol or 2-alkylphenols with 2-alkyl-1-alkenes and/or 2-aryl-1-alkenes in the liquid phase, optionally in the presence of inert diluents and/or an excess of the alkene, wherein the reaction is carried out in the presence of modified aluminum-containing catalysts obtained by adding small amounts of polyhalophenols, each having at least 3 like or unlike halogen substituents from the group of the elements fluorine, chlorine, and bromine, serving as cocatalysts, to known aluminum trisphenolate catalysts, wherein the molar ratio between the cocatalysts and the aluminum compound is in the range 0.5:1–8:1.

The invention also relates to the catalyst for manufacturing the ortho-alkylated phenols, which catalyst is comprised of the (2-alkyl)phenol undergoing alkylation, an organoaluminum compound, and a polyhalophenol as the (or a) cocatalyst.

11 Claims, No Drawings

METHOD OF MANUFACTURING ORTHO-SUBSTITUTED ALKYLPHENOLS, AND CATALYST THEREFOR

BACKGROUND OF THE INVENTION

1. Field of the Invention

The invention relates to a method of manufacturing alkylphenols using a highly active aluminum-containing homogeneous catalyst and the catalyst itself. In particular, the present invention relates to a method of manufacturing alkylphenols wherein alkylation of phenol, or particularly of 2-alkylphenols by an alkene proceeds more rapidly, and at lower temperatures and pressures, than with ordinary aluminum phenolate catalysts.

2. Discussion of the Background

Ortho-substituted and di-ortho-substituted alkylphenols can be obtained by addition of alkenes to phenol, 2-alkylphenols, and other hydroxyaromatics, in the presence of aluminum phenolates (see Ullmann, 1979, "Enzyklopaedie der Technischen Chemie", V. 18, pp. 200 ff.). Ordinarily these reactions occur at a temperature of at least 100° C. and possibly under elevated pressure. The optimal temperature region which is selected in each case depends on the groups connected to the C=C bond in the alkene which is undergoing chemical addition. The alkyl group formed is always branched to a very high degree (see Ullmann, loc.cit.). Isobutene and other alkenes which lead to formation of tertiary alkyl substituents are particularly reactive. Thus, the addition of isobutene to phenol or 2-tert-butylphenol is generally carried out at 110°-120° C. under an elevated pressure of up to 25 bar, whereas for alkenes such as propene, cyclopentene, or cyclohexene, reaction temperatures of >180° C. are required.

The aluminum phenolate catalyst is obtained by dissolving 1-3 wt. % aluminum in the phenol which is to be alkylated (see U.S. Pat. No. 2,831,898, Ger. Pats. 944,014 and 1,044,825; *J. Org. Chem.*, 22, 1957, 642; and *Anqew. Chem.*, 69, 1957, 699). It can also be obtained by reacting aluminum alcoholates or organoaluminum compounds with the phenol, or by other methods. The aluminum phenolates are known to have the highest selectivity and activity among the number of metal phenolates discussed in the patent literature. However, they also must be used in relatively large amounts in order to achieve economically important space yields per unit time.

Another disadvantage of the known methods is that prior to distilling the reaction product, one must deactivate the large amounts of the only moderately active aluminum trisphenolate catalyst. Environmentally safe disposal of the resulting wastewaters containing aluminum compounds and (alkyl)phenols presents further problems. An indication of the importance of this is the number of patent applications which have been and continue to be filed which are concerned with deactivation of the catalysts and decontaminating the wastewaters and/or reducing the amount of wastes (see, e.g., U.S. Pat. No. 3,200,157, Ger. Pat. 1,809,555, Ger. OS 20 039 062, U.S. Pat. No. 3,939,215, Ger. Pat. 26 02 149, Belg. Pat. 842,691, and U.S. Pat. Nos. 3,652,685 and 3,970,708). The problems associated with wastewater disposal have not been solved by changing to heterogeneous versions of the known catalysts (see Eur. Pat. 0,206,085), because the catalytically active aluminum phenolate catalysts are still carried away with the reaction products, in significant amounts.

There have been only a few proposals of measures for increasing the above-mentioned moderately low activity of the aluminum trisphenolate catalysts to any appreciable degree. The addition of metal halides, in particular alkali chlorides, earth alkali chlorides, and aluminum chlorides has been reported as advantageous (Ger. Pat. 1,044,825). Additionally, the use of alkyl halides (U.S. Pat. Nos. 3,426,082 and 3,200,157), alkali phenolates (Fr. Pat. 1,331,450, and Jap. OS 61-000,036 (in CA 104, 1986:186,127)), and cocatalysts comprising nitrogen and/or phosphorus (Jap. OS 60-218,346 in CA 104, 1986:88,273) can be effective. However, these examples suffer from the disadvantages of requiring unchanged high reaction temperature and/or pressures and of producing increased amounts of undesirable para-alkylphenol isomers. Thus the above-mentioned additives have not achieved any appreciable commercial success.

The only case of a catalyst active below 100° C. is that of organoaluminum compounds, particularly alkylaluminums, combined with 2-tert-butylphenol (U.S. Pat. No. 3,355,504). With this system, isobutene is chemically added to 2-tert-butylphenol (used instead of phenol), at temperatures as low as 10° C. Despite the low reaction temperature, the alkylation proceeds rapidly, to give the desired 2,6-di-tert-butylphenol, with relatively small amounts of undesired byproducts, such as 2,4-di-tert-butylphenol and 2,4,6-tri-tert-butylphenol while using amounts of catalyst comparable to the amounts of the higher temperature catalysts mentioned above (c. 1-3 mol % based on the amount of 2-tert-butylphenol used). However, as with other known phenol alkylation catalysts, this special system must be deactivated prior to product refinement. Otherwise dealkylation and transalkylation occur during the distillation.

The selectivity, yield and economic efficiency of the formation of 2,6-di-tert-butylphenol from phenol and/or 2-tert-butylphenol may be substantially increased above that offered by the above-mentioned state of the art, by various known methods (Eur. OSS 0,347,709 and 0,347,710, and especially Ger. Pat. 39 41 472). In each case the use of the known catalysts is recommended.

Most of the state of the art methods use catalysts having relatively low activity, which require the use of high temperatures. This results in the following disadvantages: large amounts of undesired byproducts and difficulty in disposal of large amounts of deactivated catalyst.

SUMMARY OF THE INVENTION

Accordingly, one object of the present invention is to provide a catalyst having improved activity for the manufacture of ortho-substituted alkylphenols.

A further object of the present invention is to provide a catalyst which may be used in lower quantities than conventional catalysts in the production of ortho-substituted phenols.

Another object of the present invention is to provide a catalyst which will allow the production of ortho alkylphenols at high rates of production even at low temperatures.

A still further object of the present invention is to provide a method for production of ortho alkylphenols which can be performed at low temperatures at high rates of production using a catalyst which can be used at lower levels than conventional catalysts.

A further object of the present invention is to provide a catalyst for production of ortho alkylphenols which may be disposed of in an environmentally safe manner with a minimum amount of effort.

These and other objects and attendant advantages have been satisfied by the discovery of a method of preparing an ortho-substituted alkylphenol, particularly suitable for manufacturing 2,6-dialkylphenols, such as 2,6-di-tert-butylphenol, or novel compounds such as 2-cyclooctyl-6-tert-butylphenol, wherein the method comprises: reacting a phenol or a 2-alkylphenol with a 2-alkyl-1-alkene or 2-aryl-1-alkene or both in the liquid phase, at a temperature of from 0° to 100° C. and a pressure of from 0.1 to 20 bar; wherein the reaction is carried out in the presence of a modified aluminum-containing catalyst prepared by a method comprising adding a small amount of one or more polyhalophenols as cocatalyst, to one or more aluminum trisphenolate catalysts, wherein the polyhalophenols each have at least 3 halogen substituents, which may be the same or different, and are selected from the group consisting of fluorine, chlorine, and bromine and wherein the catalyst is formed in the presence of the cocatalyst, or the cocatalyst is added to the already formed catalyst prior to the start of the alkylation reaction, in an amount such that the molar ratio between the cocatalyst and the aluminum compound is from 0.5:1–8:1, more preferred 1:1–6:1 and most preferred 2:1–3:1.

DETAILED DESCRIPTION OF THE PREFERRED EMBODIMENTS

The present invention relates to a method of preparing an ortho-substituted alkylphenol, comprising: reacting a phenol or a 2-alkylphenol with a 2-alkyl-1-alkene or a 2-aryl-1-alkene or both in the liquid phase, at a temperature of from 0° to 100° C. and a pressure of from 0.1 to 20 bar; wherein the reaction is carried out in the presence of a modified aluminum-containing catalyst prepared by a method comprising adding a small amount of one or more polyhalophenols as cocatalyst, to one or more aluminum trisphenolate catalysts, wherein the polyhalophenols each have at least 3 halogen substituents, which may be the same or different, and are selected from the group consisting of fluorine, chlorine, and bromine; wherein the catalyst is formed in the presence of the cocatalyst, or the cocatalyst is added to the already formed catalyst prior to the start of the reaction step, in an amount such that the molar ratio between the cocatalyst and the aluminum compound is from 0.5:1–8:1.

The present invention further relates to a catalyst for producing an ortho-alkylated phenol, comprising:
 a) the (2-alkyl-)phenol which is undergoing alkylation;
 b) a polyhalophenol as cocatalyst; and
 c) an organoaluminum compound of formula (I):

$$AlR_{(3-n)}X_n \qquad (I)$$

where n is 0 or 1, R represents an alkyl group having from 1 to 4 C atoms, and X represents chlorine, bromine or hydrogen; and wherein catalyst components (b) and (c) are present in a molar ratio of from 0.5:1–8:1 and preferably is 2:1–3:1.

The method of the present invention is performed in the liquid phase and may optionally be performed in the presence of suitable inert diluents or an excess of the alkene reactant which is being used as alkylating agent or both. Suitable inert diluents include aliphatic or cycloaliphatic hydrocarbons having 5–10 carbon atoms. Particularly preferred diluents are saturated aliphatic or cycloaliphatic hydrocarbons, such as hexane, cyclohexane, ethylcyclohexane, isopropylcyclohexane (hydrocumene), or decalin. The inert diluents, which can be in liquid or dissolved form, are used in amounts of 20–1.000 parts by weight (pbw), preferably 40–500 pbw, most preferably 60–200 pbw, per 100 pbw (2-alkyl)-phenol. When a diluent and an excess of the alkene is used, the alkene is used in an excess of 0,1–10 mol per mol 2-(alkyl)phenol; when as diluent only alkene is used, then the alkene is used in an excess of 2–10 mol per mol 2-(alkyl)phenol.

The method is particularly suitable for manufacturing 2,6-dialkylphenols, particularly 2,6-di-tert-butylphenol, or novel compounds such as 2-cyclooctyl-6-tert-butylphenol.

The present method is very advantageous because the addition of the selected polyhalophenols serving as cocatalysts, to the aluminum phenolate catalyst which is being modified, preferably prior to the formation of the catalyst, leads to increased catalyst activity in the alkylation of phenol or 2-alkylphenols. This results in a higher reaction rate with no increase in the amount of catalyst used, and production of the desired substituted phenols in shorter times and/or with less catalyst.

The alkylphenols of the present invention may contain secondary or tertiary (cyclo)alkyl ortho-substituents, or both, having 3–10 C atoms, preferably 4–8 C atoms, most preferably 4–7 C atoms.

The alkylating agents of the present invention are 2-alkyl-1-alkenes, 2-aryl-1-alkenes or both. The substituted alkenes include alkenes having 2–10 C atoms, preferably 4–8 C atoms, most preferable 4–7 C atoms in the alkene backbone with sustituents which are alkyl groups of 1 to 10 C atoms, preferably 1–6 C atoms, and mono-, di-, and tri-cyclic hydrocarbon aryl groups, preferably mono- and ci-cyclic hydrocarbon aryl groups. Preferred alkylating agents include isobutene and alpha-methylstyrene.

The present method allows the manufacture of 2,6-dialkylphenols under mild conditions, such as low reaction temperature and pressure, from phenols or 2-alkylphenols, with the alkylating agents being 2-alkyl-1-alkenes and/or 2-aryl-1-alkenes (1,1-dialkylethylenes and/or 1-aryl-1-alkylethylenes), in the presence of a modified, cocatalyst-containing aluminum trisphenolate catalyst.

The modified aluminum trisphenolate catalysts are used in amounts of 0.005–5 mol %, preferably 0.05–0.8 mol %, most preferably 0.1–0.5 mol %, based on the (2-alkyl)phenol used.

The 2-alkyl-1-alkenes and/or 2-aryl-1-alkenes are added to the reaction mixture at temperatures of 0°–100° C., preferably 10°–80° C., most preferably 15°–50° C., and pressures of 0.1–20 bar, preferably 0.2–6.0 bar, most preferably 0.5–3.5 bar.

The modified aluminum trisphenolate catalysts are produced by addition, prior to the start of the alkylation, of 0.5–8 mol, preferably 1.0–6.0 mol, most preferably 2.0–3.0 mol of one or more polyhalophenols per mol of unmodified catalyst in the (2-alkyl)phenol, with the appropriate amounts of the 2-alkyl-1-alkenes and/or 2-aryl-1-alkenes being charged subsequently.

The polyhalophenols comprising the cocatalyst contain fluorine, chlorine, bromine or mixtures thereof, such that each of the polyhalophenols have at least 3 and preferably 5 like or unlike halogen substituents. Preferred polyhalophenol cocatalysts include 2,4,6-trichlorophenol, pentafluorophenol, pentachlorophenol, and pentabromophenol, with pentachlorophenol being most preferred.

The degree of increase in activity in the catalyst of the present invention is affected not only by the molar ratio of cocatalyst to aluminum trisphenolate catalyst, but also by the nature of the cocatalyst employed, and by the structures of the (2-alkyl)phenol and alkene reactants. Accordingly, in individual cases the optimal conditions of molar ratio and reaction temperature and pressure should be determined experimentally. Such determinations are well within the abilities of one of ordinary skill in the art and is exemplified in the Examples which follow.

The catalyst composition of the present invention is formed by adding the prescribed amount of cocatalyst to the (2-alkyl)phenol, which may be dissolved in a diluent, then adding the organoaluminum compound, prior to initiating the alkylation by adding the alkene. Alternatively, the catalyst modification may be carried out by allowing the cocatalyst to interact with a catalyst already produced from (2-alkyl)phenol and aluminum compounds.

The temperature during catalyst formation is not critical, but it is advantageous not to exceed the temperature required for the alkylation, and preferably the organoaluminum components should be added at room temperature or below.

All of the materials used in the method of the present invention, such as the (2-alkyl)phenol to be alkylated, all of the associated alkenes, and all of the diluents which optionally may be used, must be free of water and catalyst poisons.

The ortho-disubstituted phenol products which can be manufactured according to the invention are compounds which may be precursors of compounds useful in areas such as phenolic antioxidants or pharmaceuticals.

Having generally described this invention, a further understanding can be obtained by reference to certain specific examples which are provided herein for purposes of illustration only and are not intended to be limiting unless otherwise specified.

The method of the present invention is illustrated in more detail by the following Examples:

EXAMPLES

The alkylations of phenol or 2-alkylphenols were carried out with isobutene (as an example of a 2-alkyl-1-alkene) in a stirred autoclave at a maximum stirrer rpm of <1400 rpm. Temperature control of the reactor was maintained by a high-powered temperature controller. A temperature sensor placed in the interior of the reactor allowed monitoring of the reaction temperature. A suitable measuring device was provided to allow reactor level changes to be monitored. Samples were taken for gas chromatographic analysis via a nipple on the reactor. Prior to determination of the proportions of the various components of the reaction mixture by GC, the catalyst contained in the sample was deactivated by addition of a few drops of water. Extraneous solvents which might be present are not in the following Tables. The data relating to the various Examples represent the compositions (in wt. %) of the reaction mixtures without such solvents ("solvent-free").

For all of the alkylations involved in the Examples, the stated amount of the (2-alkyl)phenol was charged to the dry stirred-autoclave, followed by the stated amount (if any) of the solvent. The prescribed amount of cocatalyst was then added, and air, particularly residual oxygen, was removed from the reaction mixture and reactor by purging with inert gas. The desired amount of catalyst was formed by adding triethylaluminum dissolved in (cyclo)aliphatic hydrocarbons, at $\leq 30°$ C. After the liberated ethane was removed, the reactor was closed and its contents were brought to temperature. Then, at the desired reaction temperature and under vigorous mixing, isobutene was added portionwise in the specified amount. The isothermally conducted alkylation was generally terminated as soon as no appreciable decrease in the content of the (2-alkyl)phenol employed could be observed by GC, or as soon as a high concentration of 2-alkyl-6-tert-butylphenol was reached.

Because the catalyst system was used only in small amounts and is sensitive to certain impurities, comparison tests are possible only within a series of tests using the same charges of the main feedstock, the solvent, the activator, and triethylaluminum, which charges do not change during the tests. This was ensured by control tests.

In the Tables in each case the total amounts of (2-alkyl)phenol and isobutene used are given. The pressure stated in units of bar is the total system pressure (absolute pressure).

EXAMPLES 1–4

Example 1 is a Comparative Example which is not in accordance with the present invention (see Table I).

By the method described above, 251 g (1.67 mol) 2-tert-butylphenol (2-TBP) was reacted at 1.5 bar and 10° C. with 1.9–2.0 mol isobutene in the presence of 5.8 mol aluminum tris(2-tert-butylphenolate). In Examples 2–4, in accordance with the present invention, 11.8 mmol of the indicated cocatalyst was present. The samples taken after the indicated reaction times showed that 2-TBP is consumed faster in the presence of the cocatalysts than in the Comparison Example 1 (see Table 1), and is converted to 2,6-di-tert-butylphenol (2,6-DTBP) and, to a much lesser degree, to 2,4,6-tri-tert-butylphenol (2,4,6-TTBP) and other byproducts.

EXAMPLES 5–18

Examples 5 and 14 are Comparative Examples and are not in accordance with the present invention (see Table II for Exs. 5–13 and Table III for Exs. 14–18).

By the method used in Examples 1–4, 200 ml cyclohexane was added to 251 g (1.67 mol) 2-TBP and the 2-TBP was reacted with isobutene present in excess (2.1–2.6 mol in the tests of Table II, and 2.7–3.0 mol in the tests of Table III) in the presence of 5.8 mmol of the aluminum-containing alkylation catalyst, at 10° C. and 1.5 or 1.6 bar. In addition to the cyclohexane diluent, in Examples 6–13 and 15–18, in accordance with the present invention, the cocatalysts indicated in Tables II and III were added in the specified molar ratios based on the indicated amounts of aluminum-containing catalysts, with the cocatalyst addition being prior to catalyst formation.

It is seen that the reaction of 2-tert-butylphenol in the presence of the diluent proceeds more rapidly when the cocatalysts are present, and thus 2,6-DTBP can be produced at a relatively high rate according to the present method despite the use of a low reaction temperature and a small amount of catalyst. The addition of the diluent and/or increased excess isobutene results in much less 2,4,6-tri-tert-butylphenol in the product mixture than when no diluent is present (see Table I), and for comparable conversions of 2-TBP and comparable ratios of cocatalyst to aluminum. Thus the selectivity of formation of 2,6-DTBP is increased, which is important to the economics of the manufacturing process.

EXAMPLES 19-25

Examples 19 and 23 are Comparative Examples and are not in accordance with the present invention (see Table IV).

The main feedstock was dissolved in the specified amount of diluent (viz. 200 ml cyclohexane), and then, by the method described above, 257 g (1.67 mol) 2-TBP was reacted with excess isobutene at 1.7 bar and 30° or 50° C. In the examples according to the invention, the amounts of the various cocatalysts indicated in Table IV were added prior to catalyst formation (by addition of 5.8 mmol triethylaluminum).

Comparison of the results of Examples 20-22 and 24-25 of the present invention with Comparative Examples 19 and 23, carried out without addition of the cocatalysts, indicates the effectiveness of the proposed activators at reaction temperatures above those used in Examples 1-18.

EXAMPLES 26-33

Examples 26, 32, and 33 are Comparative Examples and are not in accordance with the present invention (see Table V).

By the method used in Examples 1-25, 251 g (1.67 mol) 2-TBP was reacted with isobutene present in excess, in the presence of 200 ml cyclohexane after addition of the amounts of fluorine-containing compounds set forth in Table V and catalyst formation with 5.8 mmol triethylaluminum, at 1.5 bar and 10° C.

The results demonstrate that, using as a basis for comparison the composition of the reaction mixture achieved at various reaction times in the presence of an unmodified catalyst (Example 26), the rate of conversion is greater in Examples 27-31 of the present invention, and this is reflected in high conversions of the 2-TBP. On the other hand, the Comparison Examples 32 and 33 indicate that increases in catalyst activity which had been observed in the presence of certain polyhalophenols were not observed for other, similar compounds, when the other compounds are present in comparable molar amounts. Even with compounds of very similar structure, the addition of even small amounts can result in a decrease in catalyst activity.

EXAMPLES 34-38

Example 34 is a comparative Example and is not in accordance with the present invention (see Table VI).

By the method used in Examples 1-33, 171 g (0.83 mol) 2,4-di-tert-butylphenol (2,4-DTBP) was dissolved in 350 ml hexane, and the amount (if any) of various polyhalophenols indicated in Table VI was added to the mixture, followed by addition of 5.8 mmol triethylaluminum to said mixture, at room temperature. The 2,4-DTBP was then reacted with 1.2-1.6 mol isobutene at 1.7 bar and 30° C., to form 2,4,6-tri-tert-butylphenol (2,4,6-TTBP).

The compositions presented in Table VI of the samples taken after various reaction times demonstrate that the inventively modified catalysts also substantially accelerate the rate of alkylation of 2,4-DTBP with isobutene. The use of the different diluent does not diminish the effect.

EXAMPLES 39-45

Examples 39 and 41 are Comparative Examples and are not in accordance with the present invention (see Table VII).

By the method described above, 102.2 g (0.5 mol) 2-cyclooctylphenol was diluted with 100 ml cyclohexane, and 1.7 mmol of alkylation catalyst was formed in the reaction mixture (by adding 1.7 mmol triethylaluminum), and where specified in the presence of the specified inventive cocatalysts. Then the reaction of the main feedstock with isobutene present in excess, to form 2-cyclooctyl-6-tert-butylphenol, was carried out at 1.9 bar and the temperatures indicated in Table VII. This compound was previously unknown.

It is seen from the contents of 2-cyclooctylphenol given in Table VII that the alkylation can be substantially accelerated at 10° C. as well as at 30° C., by modifying the catalyst with pentachlorophenol, so that relatively high concentrations of the 2,6-dialkylphenol (2-cyclooctyl-6-tert-butylphenol) can be obtained quite rapidly and therefore more economically.

EXAMPLES 46-51

Example 46 is a Comparative Example and is not in accordance with the present invention (see Table VIII).

By the method used in Examples 1-45, 2-cyclohexylphenol was alkylated with isobutene present in excess, at 30° C. The reactions were carried out at 2.2 bar and the stated amounts (Table VIII) of main feedstock, diluent, aluminum-containing catalyst (possibly modified with pentafluorophenol or pentachlorophenol, where specified), and alkene.

The compositions of the samples taken after various reaction times demonstrate the advantageous catalyst-modifying effect of the added cocatalysts of the present invention.

EXAMPLES 52-57

Examples 52 and 55 are Comparative Examples and are not in accordance with the present invention (see Table IX).

By the method described above, 1.0 mol 2-isopropylphenol (136.2 g) or phenol (94.1 g) was alkylated with isobutene present in excess, in the presence of a catalyst formed by addition of 3.4 mmol triethylaluminum (which catalyst was possibly modified with pentachlorophenol, where specified and in the amounts specified in Table IX), at 50° or 10° C. Despite the slow rates of the reactions with 2-isopropylphenol, and of the reactions with phenol diluted with cyclohexane at 50° C., the presence of pentachlorophenol as a cocatalyst had a significant accelerating effect.

Obviously, numerous modifications and variations of the present invention are possible in light of the above teachings. It is therefore to be understood that within the scope of the appended claims, the invention may be practiced otherwise than as specifically described herein.

TABLE I

| Example No. | Cocatalyst | Molar ratio of cocatalyst to triethyl-aluminum | Reaction time (min) | Composition of the reaction mixture (%, determined by GC) | | |
|---|---|---|---|---|---|---|
| | | | | 2-TBP | 2,6-DTBP | 2,4,6-TTBP |
| 1 | None (Comparison Example) | — | 30 | 46.5 | 50.0 | 2.1 |
| | | | 40 | 34.7 | 61.2 | 2.8 |
| | | | 60 | 19.9 | 75.5 | 3.8 |
| | | | 75 | 13.3 | 81.9 | 4.1 |
| | | | 90 | 9.1 | 86.0 | 4.3 |
| | | | 120 | 5.2 | 89.3 | 4.8 |
| | | | 180 | 2.1 | 92.5 | 4.9 |
| 2 | 2,4,6-Trichloro-phenol (TCP) | 2:1 | 30 | 40.0 | 55.6 | 2.5 |
| | | | 40 | 28.0 | 67.0 | 3.3 |
| | | | 60 | 13.2 | 81.7 | 4.0 |
| | | | 75 | 6.0 | 88.7 | 4.4 |
| | | | 90 | 2.1 | 92.7 | 4.5 |
| | | | 120 | 0.7 | 93.7 | 4.7 |
| | | | 180 | 0.7 | 93.7 | 4.9 |
| 3 | 2,4,6-Tribromo-phenol (TBRP) | 2:1 | 30 | 39.4 | 55.9 | 2.9 |
| | | | 40 | 26.6 | 67.9 | 3.8 |
| | | | 60 | 10.7 | 83.3 | 4.8 |
| | | | 75 | 2.8 | 90.9 | 5.2 |
| | | | 90 | 1.3 | 92.5 | 5.3 |
| | | | 120 | 1.1 | 92.6 | 5.5 |
| | | | 180 | 1.0 | 92.2 | 5.9 |
| 4 | Pentachloro-phenol (PCP) | 2:1 | 30 | 40.5 | 52.8 | 4.4 |
| | | | 40 | 24.8 | 66.7 | 6.5 |
| | | | 60 | 6.2 | 83.8 | 9.0 |
| | | | 75 | 0.8 | 88.9 | 9.3 |
| | | | 90 | 0.5 | 88.7 | 9.9 |
| | | | 120 | 0.5 | 88.2 | 10.2 |
| | | | 180 | 0.5 | 87.4 | 11.1 |

NB: All reactions employed 251 g (1.67 mol) 2-TBP, 5.8 mmol triethylaluminum (1.02 molar in hexane), and 1.9–2,0 mol isobutene, at pressure 1.5 bar.

TABLE II

Alkylation of 2-TBP with isobutene at 10° C. in the presence of various polyhalophenols. (Tests with addition of a diluent)

| Example No. | Cocatalyst | Molar ratio of cocatalyst to triethyl-aluminum | Reaction time (min) | Composition of the reaction mixture (%, determined by GC) | | |
|---|---|---|---|---|---|---|
| | | | | 2-TBP | 2,6-DTBP | 2,4,6-TTBP |
| 5 | None (Comparison Example) | — | 30 | 59.2 | 39.9 | 0.4 |
| | | | 40 | 48.2 | 50.6 | 0.6 |
| | | | 60 | 34.0 | 64.6 | 0.9 |
| | | | 75 | 25.9 | 73.0 | 1.1 |
| | | | 90 | 21.5 | 77.0 | 1.2 |
| | | | 120 | 14.3 | 83.9 | 1.4 |
| | | | 180 | 7.7 | 90.4 | 1.6 |
| 6 | 2,4,6-Tichloro-phenol (TCP) | 2:1 | 30 | 55.8 | 42.7 | 0.4 |
| | | | 40 | 45.9 | 52.6 | 0.6 |
| | | | 60 | 30.8 | 67.3 | 0.9 |
| | | | 75 | 21.4 | 76.6 | 1.1 |
| | | | 90 | 17.2 | 80.9 | 1.2 |
| | | | 120 | 9.6 | 88.4 | 1.4 |
| | | | 180 | 3.5 | 94.2 | 1.6 |
| 7 | | 3:1 | 30 | 51.6 | 47.0 | 0.5 |
| | | | 40 | 39.1 | 58.7 | 0.7 |
| | | | 60 | 24.0 | 74.1 | 1.0 |
| | | | 75 | 14.6 | 83.3 | 1.2 |
| | | | 90 | 10.5 | 87.3 | 1.3 |
| | | | 120 | 4.1 | 93.6 | 1.5 |
| | | | 180 | 1.3 | 96.5 | 1.5 |
| 8 | | 4:1 | 30 | 59.6 | 38.7 | 0.3 |
| | | | 40 | 49.3 | 49.1 | 0.5 |
| | | | 60 | 33.2 | 64.8 | 0.8 |
| | | | 75 | 23.4 | 74.4 | 1.0 |
| | | | 90 | 17.1 | 80.6 | 1.2 |
| | | | 120 | 8.6 | 89.0 | 1.4 |
| | | | 180 | 2.3 | 95.2 | 1.6 |
| 9 | 2,4,6-Tribromo-phenol | 2:1 | 60 | 59.2 | 39.6 | 0.4 |
| | | | 75 | 33.0 | 65.3 | 1.0 |
| | | | 90 | 24.4 | 73.5 | 1.2 |
| | | | 120 | 18.4 | 79.5 | 1.3 |
| | | | 180 | 9.1 | 88.6 | 1.6 |
| | | | 120 | 1.7 | 95.9 | 1.8 |
| | | | 180 | | | |

TABLE II-continued

Alkylation of 2-TBP with isobutene at 10° C. in the presence of various polyhalophenols. (Tests with addition of a diluent)

| Example No. | Cocatalyst | Molar ratio of cocatalyst to triethyl-aluminum | Reaction time (min) | Composition of the reaction mixture (%, determined by GC) | | |
|---|---|---|---|---|---|---|
| | | | | 2-TBP | 2,6-DTBP | 2,4,6-TTBP |
| 10 | | 3:1 | 30 | 64.2 | 34.4 | 0.4 |
| | | | 60 | 40.1 | 57.9 | 0.8 |
| | | | 75 | 29.6 | 68.3 | 1.1 |
| | | | 90 | 22.6 | 75.0 | 1.3 |
| | | | 120 | 13.2 | 84.6 | 1.5 |
| | | | 180 | 2.7 | 94.6 | 1.9 |
| 11 | Pentachloro-phenol (PCP) | 1:1 | 30 | 46.3 | 52.2 | 0.8 |
| | | | 40 | 35.2 | 63.0 | 1.1 |
| | | | 60 | 19.2 | 78.8 | 1.6 |
| | | | 75 | 9.9 | 87.6 | 2.0 |
| | | | 90 | 5.5 | 91.8 | 2.3 |
| | | | 120 | 1.2 | 95.7 | 2.7 |
| | | | 180 | 0.8 | 95.9 | 2.9 |
| 12 | | 2:1 | 30 | 40.8 | 57.0 | 1.3 |
| | | | 40 | 24.6 | 72.7 | 2.0 |
| | | | 60 | 4.5 | 91.8 | 3.2 |
| | | | 75 | 0.6 | 95.2 | 3.7 |
| | | | 90 | 0.7 | 95.0 | 3.7 |
| | | | 120 | 0.8 | 94.5 | 4.2 |
| | | | 180 | 0.6 | 94.0 | 4.9 |
| | | | 360 | 0.6 | 92.2 | 6.6 |
| 13 | | 3:1 | 30 | 24.7 | 71.8 | 2.9 |
| | | | 40 | 9.1 | 86.1 | 4.0 |
| | | | 60 | 0.6 | 93.1 | 5.6 |
| | | | 75 | 0.4 | 92.1 | 6.6 |
| | | | 90 | 0.4 | 91.5 | 7.2 |
| | | | 120 | 0.5 | 90.3 | 8.4 |
| | | | 180 | 0.4 | 88.1 | 10.7 |
| | | | 360 | 0.6 | 81.9 | 16.2 |

NB: All reactions employed 251 g (1.67 mol) 2-TBP, 5.8 mmol triethylaluminum, 200 ml cyclohexane, and 2.1–2.6 mol isobutene, at pressure 1.5 bar. Temperature was 10° C.

TABLE III

Alkylation of 2-TBP with isobutene at 10° C. in the presence of various polyhalophenols. (Tests with addition of a diluent)

| Example No. | Cocatalyst | Molar ratio of cocatalyst to triethyl-aluminum | Reaction time (min) | Composition of the reaction mixture (%, determined by GC) | | |
|---|---|---|---|---|---|---|
| | | | | 2-TBP | 2,6-DTBP | 2,4,6-TTBP |
| 14 | None (Comparison Example) | — | 30 | 65.2 | 34.0 | 0.4 |
| | | | 60 | 38.6 | 60.1 | 0.8 |
| | | | 75 | 30.1 | 68.6 | 1.0 |
| | | | 90 | 23.6 | 74.8 | 1.1 |
| | | | 120 | 14.1 | 84.5 | 1.3 |
| | | | 180 | 4.8 | 93.3 | 1.6 |
| | | | 360 | 0.5 | 97.4 | 1.7 |
| 15 | 2,4,6-Tribromo-phenol (TBRP) | 2:1 | 30 | 66.4 | 32.9 | 0.3 |
| | | | 60 | 38.8 | 59.8 | 0.8 |
| | | | 75 | 30.3 | 68.3 | 1.0 |
| | | | 90 | 20.8 | 77.5 | 1.2 |
| | | | 120 | 7.8 | 90.4 | 1.5 |
| | | | 180 | 0.2 | 97.6 | 1.9 |
| | | | 360 | 0.1 | 97.2 | 2.5 |
| 16 | | 4:1 | 30 | 72.8 | 26.5 | 0.2 |
| | | | 60 | 38.0 | 50.8 | 0.7 |
| | | | 75 | 35.5 | 62.9 | 0.9 |
| | | | 90 | 25.8 | 72.3 | 1.2 |
| | | | 120 | 12.4 | 85.5 | 1.6 |
| | | | 180 | 1.5 | 95.7 | 2.2 |
| | | | 360 | — | 92.5 | 7.5 |
| 17 | Pentabromo-phenol | 2:1 | 30 | 66.0 | 32.7 | 0.4 |
| | | | 40 | 54.9 | 43.8 | 0.7 |
| | | | 60 | 35.8 | 62.2 | 1.3 |
| | | | 75 | 26.3 | 71.4 | 1.6 |
| | | | 90 | 16.2 | 81.2 | 2.1 |
| | | | 120 | 3.2 | 93.6 | 2.9 |
| | | | 180 | 0.3 | 95.8 | 3.5 |
| | | | 360 | 0.1 | 95.0 | 4.5 |
| 18 | | 4:1 | 30 | 67.1 | 31.9 | 0.5 |
| | | | 40 | 58.2 | 40.6 | 0.7 |
| | | | 60 | 37.8 | 60.1 | 1.3 |

TABLE III-continued

Alkylation of 2-TBP with isobutene at 10° C. in the presence of various polyhalophenols. (Tests with addition of a diluent)

| Example No. | Cocatalyst | Molar ratio of cocatalyst to triethyl-aluminum | Reaction time (min) | Composition of the reaction mixture (%, determined by GC) | | |
|---|---|---|---|---|---|---|
| | | | | 2-TBP | 2,6-DTBP | 2,4,6-TTBP |
| | | | 75 | 24.4 | 73.0 | 1.9 |
| | | | 90 | 13.7 | 83.0 | 2.5 |
| | | | 120 | 2.4 | 93.5 | 3.3 |
| | | | 180 | 0.1 | 95.0 | 4.5 |
| | | | 360 | 0.2 | 89.8 | 9.6 |

NB: All reactions employed 251 g (1.67 mol) 2-TBP, 5.8 mmol triethylaluminum, 200 ml cyclohexane, and 2.7–3.0 mol isobutene, at pressure 1.6 bar. Temperature was 10° C.

TABLE IV

Alkylation of 2-TBP with isobutene in the presence of various polyhalophenols. (Tests with cyclohexane as a diluent, with temperature 30° C. or 50° C.)

| Example No. | Cocatalyst | Molar ratio of cocatalyst to triethyl-aluminum | Reaction temp. [°C.] | time [min] | Composition of the reaction mixture (%, determined by GC) | | |
|---|---|---|---|---|---|---|---|
| | | | | | 2-TBP | 2,6-DTBP | 2,4,6-TTBP |
| 19 | None (Comparison Example) | — | 30° | 30 | 45.7 | 52.2 | 1.1 |
| | | | | 60 | 20.7 | 76.7 | 1.9 |
| | | | | 75 | 14.8 | 82.6 | 2.1 |
| | | | | 90 | 10.5 | 85.6 | 2.6 |
| | | | | 120 | 5.5 | 91.7 | 2.5 |
| | | | | 180 | 2.7 | 94.0 | 2.8 |
| 20 | 2,4,6-Trichloro-phenol (TCP) | 5:1 | 30° | 30 | 30.4 | 66.7 | 2.0 |
| | | | | 60 | 5.6 | 90.6 | 3.0 |
| | | | | 75 | 2.7 | 93.1 | 3.4 |
| | | | | 90 | 1.1 | 93.7 | 3.9 |
| | | | | 120 | 0.2 | 93.6 | 4.9 |
| | | | | 180 | 0.2 | 91.3 | 7.6 |
| 21 | Pentachloro-phenol (PCP) | | | 30 | 5.8 | 75.1 | 15.8 |
| | | | | 60 | 0.2 | 67.3 | 30.4 |
| | | | | 75 | 0.2 | 62.6 | 35.4 |
| | | | | 90 | 0.2 | 59.5 | 38.0 |
| | | | | 120 | 0.2 | 56.1 | 41.1 |
| | | | | 180 | 0.3 | 54.8 | 43.0 |
| 22 | Pentafluoro-phenol | 3,5:1 | | 30 | 3.4 | 80.3 | 13.2 |
| | | | | 60 | 0.4 | 53.3 | 43.9 |
| | | | | 75 | 0.5 | 52.8 | 43.8 |
| | | | | 90 | 0.5 | 51.5 | 44.4 |
| | | | | 120 | 0.7 | 50.6 | 43.0 |
| | | | | 180 | 0.9 | 49.5 | 45.1 |
| 23 | None (Comparison Example) | — | 50° | 30 | 53.2 | 43.9 | 1.4 |
| | | | | 60 | 27.1 | 68.5 | 3.0 |
| | | | | 75 | 21.6 | 74.1 | 3.2 |
| | | | | 90 | 15.6 | 79.9 | 3.5 |
| | | | | 120 | 9.3 | 85.9 | 3.9 |
| | | | | 180 | 4.1 | 90.9 | 4.3 |
| 24 | 2,4,6-Trichloro-phenol (TCP) | 2:1 | | 30 | 55.6 | 41.7 | 1.0 |
| | | | | 60 | 28.8 | 67.1 | 2.4 |
| | | | | 75 | 20.1 | 75.6 | 2.9 |
| | | | | 90 | 13.4 | 82.0 | 3.3 |
| | | | | 120 | 7.5 | 87.1 | 3.4 |
| | | | | 180 | 2.6 | 92.3 | 4.2 |
| 25 | Pentachloro-phenol (PCP) | 2:1 | 50° | 30 | 41.9 | 51.0 | 3.8 |
| | | | | 60 | 11.6 | 77.0 | 8.9 |
| | | | | 75 | 5.4 | 81.6 | 10.9 |
| | | | | 90 | 2.1 | 82.3 | 13.6 |
| | | | | 120 | 0.9 | 81.7 | 15.4 |
| | | | | 180 | 0.6 | 79.0 | 18.4 |

NB: All reactions employed 251 g (1.67 mol) 2-TBP, 5.8 mmol triethylaluminum (1.02 molar in hexane), 200 ml cyclohexane, and 1.8–2.1 mol isobutene, at pressure 1.7 bar.

TABLE V

Reaction of 2-TBP with isobutene at 30° C. in the presence of various fluorine-containing compounds. (Tests with cyclohexane as a diluent)

| Example No. | Cocatalyst | Molar ratio of cocatalyst to triethyl-aluminum | Reaction time (min) | Composition of the reaction mixture (%, determined by GC) | | |
|---|---|---|---|---|---|---|
| | | | | 2-TBP | 2,6-DTBP | 2,4,6-TTBP |
| 26 | None (Comparison Example) | — | 30 | 45.9 | 52.8 | 0.7 |
| | | | 60 | 22.7 | 75.6 | 1.2 |
| | | | 75 | 16.9 | 81.3 | 1.4 |
| | | | 90 | 12.3 | 85.8 | 1.5 |
| | | | 120 | 6.9 | 91.1 | 1.6 |
| | | | 180 | 3.0 | 94.9 | 1.8 |
| 27 | Pentafluoro-phenol | 1:1.3 | 30 | 32.4 | 64.9 | 1.2 |
| | | | 60 | 7.3 | 88.9 | 2.2 |
| | | | 75 | 3.2 | 92.4 | 2.8 |
| | | | 90 | 1.7 | 93.5 | 3.1 |
| | | | 120 | 0.8 | 93.7 | 3.9 |
| | | | 180 | 0.6 | 93.3 | 4.5 |
| | | | 360 | 0.4 | 92.6 | 5.1 |
| 28 | | 1:2 | 30 | 26.5 | 70.3 | 1.4 |
| | | | 60 | 4.0 | 91.3 | 2.8 |
| | | | 75 | 1.4 | 93.4 | 3.4 |
| | | | 90 | 0.9 | 93.5 | 3.8 |
| | | | 120 | 0.6 | 93.4 | 4.2 |
| | | | 180 | 0.4 | 90.5 | 7.8 |
| 30 | 2,4-Dichloro-4-fluorophenol | 1:1 | 30 | 48.0 | 50.6 | 0.6 |
| | | | 60 | 22.0 | 76.2 | 1.1 |
| | | | 75 | 14.6 | 83.5 | 1.3 |
| | | | 90 | 10.3 | 87.8 | 1.4 |
| | | | 120 | 5.6 | 92.3 | 1.5 |
| | | | 180 | 2.0 | 95.9 | 1.7 |
| | | | 360 | 0.9 | 96.8 | 1.8 |
| 31 | | 2:1 | 30 | 47.0 | 51.6 | 0.5 |
| | | | 60 | 21.5 | 76.8 | 1.0 |
| | | | 75 | 14.7 | 83.5 | 1.1 |
| | | | 90 | 10.0 | 88.1 | 1.2 |
| | | | 120 | 4.7 | 93.4 | 1.3 |
| | | | 180 | 0.8 | 97.1 | 1.6 |
| | | | 360 | 0.7 | 97.2 | 1.6 |
| 32 | Pentafluoro-benzyl alcohol (Comparison Example) | 1:1 | 30 | 78.5 | 20.7 | 0.1 |
| | | | 60 | 61.0 | 37.9 | 0.4 |
| | | | 90 | 49.3 | 49.3 | 0.6 |
| | | | 120 | 40.0 | 58.4 | 0.8 |
| | | | 180 | 28.8 | 69.3 | 1.1 |
| 33 | | 1:2 | 30 | 94.1 | 5.2 | 0.0 |
| | | | 60 | 89.0 | 10.2 | 0.0 |
| | | | 120 | 81.2 | 18.0 | 0.1 |
| | | | 180 | 74.0 | 25.0 | 0.2 |
| | | | 360 | 59.4 | 39.4 | 0.3 |

NB: All reactions employed 251 g (1.67 mol) 2-TBP, 5.8 mmol triethylaluminum (1.02 molar in hexane), 200 ml cyclohexane, and 2.1–2.5 mol isobutene, at pressure 1.5 bar. Temperature was 10° C.

TABLE VI

Reaction of 2,4-DTBP with isobutene at 30° C. in the presence of various cocatalysts.

| Example No. | Cocatalyst | Molar ratio of cocatalyst to triethyl-aluminum | Reaction time (min) | Composition of the reaction mixture (%, determined by GC) | |
|---|---|---|---|---|---|
| | | | | 2,4-DTBP | 2,4,6-TTBP |
| 34 | None (Comparison Example) | — | 30 | 85.6 | 14.3 |
| | | | 60 | 69.2 | 30.8 |
| | | | 90 | 55.1 | 44.3 |
| | | | 120 | 43.8 | 56.0 |
| | | | 180 | 31.3 | 68.6 |
| | | | 360 | 12.7 | 87.1 |
| 35 | 2,4,6-Trichloro-phenol (TCP) | 2:1 | 30 | 81.4 | 18.1 |
| | | | 60 | 59.9 | 39.7 |
| | | | 90 | 43.6 | 55.9 |
| | | | 120 | 31.6 | 68.9 |
| | | | 180 | 17.8 | 81.6 |
| | | | 360 | 2.1 | 97.2 |
| 36 | Pentafluoro-phenol | 2:1 | 10 | 68.4 | 30.2 |
| | | | 20 | 44.3 | 53.6 |
| | | | 30 | 26.1 | 71.7 |
| | | | 45 | 6.8 | 91.2 |
| | | | 60 | 0.7 | 98.9 |
| | | | 120 | 0.6 | 99.1 |

TABLE VI-continued

Reaction of 2,4-DTBP with isobutene at 30° C. in the presence of various cocatalysts.

| Example No. | Cocatalyst | Molar ratio of cocatalyst to triethylaluminum | Reaction time (min) | Composition of the reaction mixture (%, determined by GC) | |
|---|---|---|---|---|---|
| | | | | 2,4-DTBP | 2,4,6-TTBP |
| 37 | Pentachlorophenol | 1:1 | 20 | 72.1 | 27.7 |
| | | | 30 | 57.0 | 42.9 |
| | | | 45 | 37.6 | 62.1 |
| | | | 60 | 22.6 | 77.1 |
| | | | 90 | 8.6 | 91.1 |
| | | | 120 | 3.1 | 96.7 |
| | | | 180 | 0.9 | 98.9 |
| 38 | | 2:1 | 10 | 80.2 | 19.7 |
| | | | 20 | 52.8 | 47.0 |
| | | | 30 | 27.8 | 72.0 |
| | | | 45 | 6.8 | 93.0 |
| | | | 60 | 1.3 | 98.5 |
| | | | 90 | 0.4 | 99.3 |

NB: All reactions employed 171 g (0.83 mol) 2,4-DTBP, 4.2 mmol triethylaluminum (1.02 molar in hexane), 350 ml hexane, and 1.2–1.6 mol isobutene, at pressure 1.7 bar. Temperature was 30° C.

TABLE VII

Alkylation of 2-cyclooctylphenol with isobutene in the presence of catalysts containing pentachlorophenol.

| Example No. | Molar ratio of cocatalyst of triethylaluminum | Reaction temp. [°C.] | time [min] | Composition of the reaction mixture (% determined by GC) 2-Cyclooctylphenol (2-COP) Tert-butyl ether of 2-Cyclooctylphenol (X1) 2-Cyclooctyl-6-TBP (2,6-Add.) 2-Cyclooctyl-4,6-di-tert-butylphenol (X2) | | | |
|---|---|---|---|---|---|---|---|
| | | | | 2-COP | X1 | 2,6-Add. | X2 |
| 39 | None (Comparison Example) | 10° | 2 | 95.3 | 2.0 | 2.6 | |
| | | | 4 | 93.9 | 2.5 | 3.5 | |
| | | | 6 | 89.4 | 4.8 | 5.7 | |
| 40 | 2:1 | | 1 | 94.1 | 1.9 | 3.9 | |
| | | | 2 | 89.4 | 3.6 | 70 | |
| | | | 4 | 79.8 | 7.0 | 13.2 | |
| | | | 6 | 70.4 | 10.2 | 19.1 | |
| 41 | None (Comparison Example) | 30° | 1 | 95.7 | 1.9 | 2.2 | |
| | | | 2 | 91.9 | 3.7 | 4.4 | |
| | | | 4 | 84.7 | 7.0 | 8.1 | |
| | | | 6 | 77.4 | 10.3 | 12.2 | |
| 42 | 1:1 | | 1 | 93.2 | 2.7 | 3.9 | |
| | | | 2 | 87.0 | 5.4 | 7.6 | |
| | | | 4 | 76.1 | 9.8 | 13.9 | |
| | | | 6 | 66.5 | 13.5 | 19.9 | |
| 43 | 2:1 | | 1 | 86.9 | 4.8 | 8.4 | |
| | | | 2 | 76.7 | 8.4 | 14.8 | |
| | | | 4 | 57.7 | 14.7 | 27.6 | |
| | | | 6 | 39.9 | 20.1 | 39.8 | 0.1 |
| 44 | 3:1 | | 1 | 83.3 | 5.7 | 10.8 | |
| | | | 2 | 70.9 | 8.3 | 20.6 | |
| | | | 4 | 41.6 | 19.1 | 39.2 | |
| | | | 6 | 19.7 | 23.6 | 56.1 | 0.4 |
| 45 | 4:1 | | 1 | 79.1 | 6.6 | 14.1 | |
| | | | 2 | 61.6 | 11.7 | 26.5 | 0.1 |
| | | | 4 | 29.3 | 20.8 | 49.3 | 0.3 |
| | | | 6 | 8.7 | 21.6 | 68.8 | 0.8 |

NB: All reactions employed 102.2 g (0.5 mol) 2-cyclooctylphenol, 1.7 mmol triethylaluminum, 100 ml cyclohexane, and: 1.3 mol isobutene, at pressure 1.9 bar and temperature 10° C.; or 0.7–0.8 mol isobutene, at pressure 1.9 bar and temperature 30° C.

TABLE VIII

Alkylation of 2-cyclohexylphenol with isobutene at 30° C. in the presence of modified catalysts.

Composition of the reaction mixture (%, determined by GC)
2-Cyclohexylphenol (2-CHP)
Tert-butyl ether of 2-cyclohexylphenol (X1)
2-Cyclohexyl-6-tert-butylphenol (CHTBP)
High-boiling components (probably the trisubstitution product) (X2)

| Example No. | Cocatalyst | Molar ratio of cocatalyst to triethyl-aluminum | Reaction time (min) | 2-CHP | X1 | CHTBP | X2 |
|---|---|---|---|---|---|---|---|
| 46 | None (Comparison Example) | — | 1 | 96.0 | 1.7 | 2.1 | |
| | | | 2 | 93.4 | 3.1 | 3.1 | |
| | | | 3 | 88.9 | 4.8 | 5.0 | |
| | | | 4 | 87.8 | 6.0 | 5.9 | |
| | | | 6 | 82.6 | 8.4 | 8.8 | |
| | | | MO1 | 61.8 | 18.2 | 19.5 | |
| 47 | Pentafluoro-phenol | 3,5:1 | 1 | 79.5 | 9.6 | 10.0 | |
| | | | 2 | 73.2 | 12.6 | 13.3 | |
| | | | 4 | 64.1 | 17.2 | 17.5 | |
| | | | 6 | 56.7 | 19.7 | 21.3 | |
| | | | MO1 | 33.3 | 31.1 | 34.0 | |
| 48 | Pentachloro-Phenol | 1:1 | 1 | 93.6 | 2.7 | 3.1 | |
| | | | 2 | 87.8 | 5.3 | 6.0 | |
| | | | 4 | 77.1 | 10.4 | 11.5 | |
| | | | 6 | 68.3 | 14.5 | 16.4 | |
| | | | MO1 | 36.3 | 26.8 | 36.2 | |
| 49 | | 2:1 | 1 | 90.4 | 4.0 | 5.5 | |
| | | | 2 | 81.7 | 8.0 | 10.2 | |
| | | | 4 | 64.1 | 15.4 | 20.3 | |
| | | | 6 | 47.0 | 20.8 | 28.0 | |
| | | | MO1 | 8.2 | 29.6 | 60.1 | 1.9 |
| 50 | | 4:1 | 1 | 86.7 | 5.2 | 8.0 | |
| | | | 2 | 73.0 | 10.7 | 16.3 | |
| | | | 4 | 48.1 | 19.8 | 31.6 | |
| | | | 6 | 28.3 | 24.3 | 46.7 | 0.5 |
| | | | MO1 | 0.8 | 3.5 | 87.3 | 8.1 |
| 51 | | 6:1 | 1 | 82.3 | 6.7 | 10.8 | |
| | | | 2 | 65.1 | 12.7 | 21.6 | |
| | | | 4 | 29.3 | 23.8 | 45.8 | 0.4 |
| | | | 6 | 4.9 | 24.1 | 69.1 | 1.5 |
| | | | MO1 | 0.1 | 0.3 | 28.8 | 69.8 |

NB: All reactions employed 88.2 g (0.5 mol) 2-cyclohexylphenol, 1.7 mmol triethylaluminum (1.02 molar in cyclohexane), 150 ml cyclohexane, and 0.85–1.0 mol isobutene, at pressure 2.2 bar. Temperature was 30° C. MO1 sample after 6 hrs. reaction time at 30° C. and additionally 16 hrs. at 20–25° C.

TABLE IX

Alkylation of 2-isopropylphenol or phenol, with isobutene, in the presence of pentachlorophenol-containing catalysts, at 50 or 10°.

Composition of the reaction mixture (%, determined by GC)
Main feedstock (Main)
Tert-butyl ether of 2-isopropylphenol (X1)
2-Isopropyl-6-tert-butylphenol (2,6-Add.)
Higher-boiling components (probably the trisubstitution product) (X5)

| Example No. | Main feedstock | Molar ratio of cocatalyst to triethyl-aluminum | Reaction temp. [°C.] | time [min] | Main | X1 | 2,6-Add. | X5 |
|---|---|---|---|---|---|---|---|---|
| 52 | 2-Isopro-pylphenol | None (Comparison Example) | 50° | 1 | 51.1 | 18.1 | 30.3 | 0.2 |
| | | | | 2 | 35.3 | 20.5 | 43.4 | 0.4 |
| | | | | 4 | 22.5 | 19.5 | 60.0 | 0.7 |
| | | | | 6 | 17.1 | 15.7 | 65.5 | 0.9 |
| 53 | | 2:1 | | 0.8 | 24.5 | 17.5 | 56.4 | 0.9 |
| | | | | 1.9 | 5.3 | 7.3 | 83.6 | 2.9 |
| | | | | 4 | 0.2 | 0.2 | 90.5 | 8.3 |
| | | | | 6 | 0.1 | 0.1 | 87.1 | 12.1 |
| 54 | | 2:1 | 10° | 1 | 81.9 | 6.7 | 11.1 | |
| | | | | 2 | 68.6 | 11.7 | 19.4 | 0.1 |
| | | | | 4 | 45.5 | 20.4 | 33.6 | 0.2 |
| | | | | 6 | 29.6 | 27.0 | 42.9 | 0.3 |
| 55 | Phenol | None (Comparison | | | Main Feedstock (Main) Phenyl t-butyl ether (Y1) | | | |

TABLE IX-continued

Alkylation of 2-isopropylphenol or phenol, with isobutene,
in the presence of pentachlorophenol-containing catalysts, at 50 or 10°.

| Example No. | Main feedstock | Molar ratio of cocatalyst to triethyl-aluminum | Reaction temp. [°C] | time [min] | Composition of the reaction mixture (%, determined by GC) Main feedstock (Main) Tert-butyl ether of 2-isopropylphenol (X1) 2-Isopropyl-6-tert-butylphenol (2,6-Add.) Higher-boiling components (probably the trisubstitution product) (X5) | | | |
|---|---|---|---|---|---|---|---|---|
| | | | | | Main | Y1 | 2-TBP | 2,6-DTBP |
| | | Example | 50° | 1 | 70.8 | 22.5 | 6.7 | |
| | | | | 2 | 58.8 | 31.4 | 9.6 | 0.1 |
| | | | | 4 | 46.3 | 41.6 | 11.8 | 0.2 |
| | | | | 6 | 37.5 | 48.8 | 13.0 | 0.3 |
| 56 | | 2:1 | | 1 | 69.9 | 22.7 | 7.3 | |
| | | | | 2 | 55.2 | 34.1 | 10.0 | 0.1 |
| | | | | 4 | 43.7 | 42.8 | 12.8 | 0.2 |
| | | | | 6 | 35.0 | 49.0 | 14.9 | 0.4 |
| 57 | | 4:1 | | 1 | 64.2 | 27.0 | 8.6 | 0.1 |
| | | | | 2 | 49.7 | 38.1 | 11.8 | 0.2 |
| | | | | 4 | 33.9 | 50.4 | 15.0 | 0.4 |

NB: All reactions employed 1.0 mol 2-isopropylphenol (136.2 g) or 1.0 mol phenol (94.1 g), 3.4 mmol triethylaluminum (1.02 molar in hexane), and:
1) In the case of 2-isopropylphenol as the main feedstock, 0.9–1.5 mol isobutene, at 50° C. and 2.9 bar (or 10° C. and 2.2 bar); or
2) In the case of phenol as the main feedstock, 1.5 mol isobutene and 100 ml cyclohexane, at 50° C. and 2.8 bar.

What is claimed as new and desired to be secured by Letters Patent of United States is:

1. A method of preparing an ortho-substituted alkylphenol, comprising: reacting phenol or a 2-($C_{3-10}$)alkyl-phenol with a 2-alkyl-1-alkene or a 2-aryl-1-alkene in the liquid phase, at a temperature of from 1° to 100° C. and a pressure of from 0.1 to 20 bar; wherein the reaction is carried out in the presence of a modified aluminum-containing catalyst prepared by a method comprising adding a small amount of one or more polyhalophenol as a cocatalyst to one or more aluminum tris(2-alkyl-)phenolate catalysts, wherein said one or more polyhalophenols each have at least 3 halogen substituents, which may be the same or different, and are selected from the group consisting of fluorine, chlorine, and bromine; wherein the catalyst is formed in the presence of the cocatalyst, or the cocatalyst is added to the already formed catalyst prior to the start of the reaction step, in an amount such that the molar ratio between the cocatalyst and the aluminum compound is from 0.5:1 to 8:1.

2. The method of claim 1, wherein said one or more polyhalophenols each have 5 halogen substituents.

3. The method of claim 1, wherein said molar ratio between the cocatalyst and the aluminum compound is from 1:1 to 6:1.

4. The method of claim 1, wherein said molar ratio between the cocatalyst and the aluminum compound is from 2:1 to 3:1.

5. The method of claim 1, wherein 2,6-di-tert-butyl-phenol is prepared.

6. The method of claim 1, wherein 2-cyclooctyl-6-tert-butylphenol is prepared.

7. The method of claim 1, wherein said phenol or said 2-($C_{3-10}$)alkyl-phenol is reacted with said alkene in the liquid phase, in the presence of an inert diluent.

8. The method of claim 7, wherein an excess of said alkene is used.

9. The method of claim 1, wherein said phenol or said 2-($C_{3-10}$)alkyl-phenol is reacted with said alkene in the liquid phase, in the presence of an excess of said alkene.

10. The method of claim 1, wherein said inert diluent is one member selected from the group consisting of saturated aliphatic and cycloaliphatic hydrocarbons.

11. The method of claim 1, wherein said inert diluent is hexane, cyclohexane, ethylcyclohexane, isopropylcyclohexane or decalin.

* * * * *